US008927012B2

(12) United States Patent
Bubnis et al.

(10) Patent No.: US 8,927,012 B2
(45) Date of Patent: Jan. 6, 2015

(54) MULTI-VITAMIN AND MINERAL NUTRITIONAL SUPPLEMENTS (71) Applicant: Wyeth LLC, New York, NY (US)

(72) Inventors: William Bubnis, Mechanicsville, VA (US); Richard Cotter, Mendham, NJ (US); Paul W. Herman, Bridgewater, NJ (US); Judith Moreines, Edgewater, NJ (US); Scott W. Poxon, Mechanicsville, VA (US); Bruce W. Sutton, Richmond, VA (US); Jeffrey V. Vernon, Fredericksburg, VA (US); Denise L. Walters, Richmond, VA (US); Michael G. Williams, Midlothian, VA (US); Neil Wittenberg, Randolph, NJ (US)

(73) Assignee: Wyeth LLC, New York, NY (US)

( * ) Notice: Subject to any disclaimer, the term of this patent is extended or adjusted under 35 U.S.C. 154(b) by 0 days.

(21) Appl. No.: 14/031,536

(22) Filed: Sep. 19, 2013

(65) Prior Publication Data
US 2014/0017312 A1  Jan. 16, 2014

Related U.S. Application Data (63) Continuation of application No. 13/023,671, filed on Feb. 9, 2011, now abandoned, which is a continuation of application No. 11/236,570, filed on Sep. 28, 2005, which is a continuation-in-part of application No. 11/090,486, filed on Mar. 28, 2005, now abandoned.

(60) Provisional application No. 60/557,247, filed on Mar. 29, 2004.

(51) Int. Cl.
A61K 31/56 (2006.01)
A61K 31/375 (2006.01)
A61K 31/525 (2006.01)
A61K 33/00 (2006.01)
A61K 31/355 (2006.01)
A61K 31/4415 (2006.01)

(52) U.S. Cl.
USPC ............ 424/464; 424/489; 424/490; 514/169

(58) Field of Classification Search
None
See application file for complete search history.

(56) References Cited

U.S. PATENT DOCUMENTS

| 3,881,005 | A | | 4/1975 | Thakkar et al. |
| 4,021,582 | A | | 5/1977 | Hsu |
| 5,571,441 | A | * | 11/1996 | Andon et al. ............ 252/1 |
| 5,654,011 | A | * | 8/1997 | Jackson et al. ............ 424/635 |
| 5,861,141 | A | | 1/1999 | Mendizabal |
| 5,869,084 | A | * | 2/1999 | Paradissis et al. ........... 424/439 |
| 5,932,561 | A | | 8/1999 | Meyers et al. |
| 6,087,353 | A | | 7/2000 | Stewart et al. |
| 6,110,502 | A | * | 8/2000 | Burruano et al. ............ 424/499 |
| 6,139,832 | A | | 10/2000 | Li et al. |
| 6,139,872 | A | | 10/2000 | Walsh |
| 6,197,832 | B1 | | 3/2001 | Sorkin |
| 6,197,862 | B1 | | 3/2001 | Asano et al. |
| 6,274,170 | B1 | * | 8/2001 | Heibel et al. ............... 424/458 |
| 6,299,896 | B1 | * | 10/2001 | Cooper et al. ............... 424/441 |
| 6,352,737 | B1 | | 3/2002 | Dolhaine et al. |
| 6,361,800 | B1 | * | 3/2002 | Cooper et al. ............... 424/630 |
| 6,376,481 | B1 | * | 4/2002 | Bruce et al. ................. 514/169 |
| 6,488,956 | B1 | * | 12/2002 | Paradissis et al. ........... 424/439 |
| 6,544,973 | B1 | | 4/2003 | Miettenen et al. |
| 6,569,453 | B2 | | 5/2003 | Linder et al. |
| 6,576,285 | B1 | | 6/2003 | Bader et al. |
| 6,589,588 | B1 | | 7/2003 | Wester et al. |
| 6,673,831 | B1 | | 1/2004 | Tobert |
| 6,953,588 | B2 | * | 10/2005 | Cooper et al. ............... 424/441 |
| 2001/0034338 | A1 | | 10/2001 | Sorkin |
| 2002/0068095 | A1 | | 6/2002 | Qi et al. |
| 2002/0103139 | A1 | | 8/2002 | Weisspapir et al. |
| 2002/0172721 | A1 | * | 11/2002 | Boulos et al. ............... 424/646 |
| 2003/0096018 | A1 | * | 5/2003 | Schloss et al. ............... 424/646 |
| 2003/0104078 | A1 | * | 6/2003 | Barrett-Reis et al. ......... 424/727 |
| 2003/0108591 | A1 | | 6/2003 | Meijer et al. |
| 2003/0133965 | A1 | | 7/2003 | Bruno et al. |
| 2003/0203854 | A1 | | 10/2003 | Pischel et al. |
| 2004/0018248 | A1 | | 1/2004 | Bendich |
| 2004/0033202 | A1 | * | 2/2004 | Cooper et al. ............... 424/46 |
| 2008/0103118 | A1 | * | 5/2008 | Clement et al. ............. 514/169 |
| 2008/0199534 | A1 | * | 8/2008 | Goldberg et al. ........... 424/602 |

FOREIGN PATENT DOCUMENTS

| DE | 20316876 U1 | 2/2004 |
| EP | 1155699 A1 | 11/2001 |
| WO | WO 99/40922 | 8/1999 |
| WO | WO99/40922 | 8/1999 |

(Continued)

OTHER PUBLICATIONS

U.S. Appl. No. 11/236,570, filed Feb. 2, 2006, Poxon, et al.
McPherson, Timothy B., et al., "Phytostanol tablets reduce human LDL-cholesterol", Journal of Pharmacy and Pharmacology, pp. 889-896, Mar. 7, 2005.

(Continued)

Primary Examiner — Robert A Wax
Assistant Examiner — Olga V Tcherkasskaya
(74) Attorney, Agent, or Firm — Maureen P. O'Brien; Jeffrey M. Gold (57) ABSTRACT The invention provides a nutritional supplement which includes micronutrients to facilitate reduction of cholesterol, and/or reduction of homocystein and/or reduction of low-density lipoprotein-cholesterol (LDL-C) oxidation in humans. In one embodiment the supplement is a multi-vitamin, a mineral supplement which includes at least one component known to reduce cholesterol. The invention further provides a method for tableting one fourth to one half of the daily effective dosage of a phytosterol containing nutritional supplement in a practical sized tablet and a method for reducing blood cholesterol in humans.

8 Claims, 3 Drawing Sheets (56) References Cited

FOREIGN PATENT DOCUMENTS

| WO | WO 00/15201 | 3/2000 |
|----|-------------|--------|
| WO | WO00/15201 | 3/2000 |
| WO | WO02/43506 | 6/2002 |
| WO | WO 02/43506 | 6/2002 |
| WO | WO03/103633 | 12/2003 |
| WO | WO 03/103633 | 12/2003 |
| WO | WO03/103640 | 12/2003 |
| WO | WO 03/103640 | 12/2003 |
| ZA | 994696 | 7/1999 |

OTHER PUBLICATIONS

Devaraj, Sridevi, et al., "Plant Sterol-Fortified Orange Juice Effectively Lowers Cholesterol Levels in Mildly Hypercholesterolemic . . . ", Arterioscler Thromb Vasc. Biol., Mar. 2004.

McCarty, M.F., "Policosanol safely down-regulates HMG-CoA reductase-potential as a component of the Esselstyn regimen", Medical Hypotheses (Dec. 19, 2001) 59(3), pp. 268-279.

Gouni-Berthold, Ioanna, et al., "Policosanol: Clinical pharmacology and therapeutic significance of a new lipid-lowering agent", American Heart Journal, vol. 143, No. 2, Aug. 29, 2001, pp. 356-365.

Fraga, Vivian, et al., "Effect of policosanol on In Vitro and In Vivo Rat Liver Microsomal Lipid Peroxidation", Archives of Medical Research, vol. 28, No. 3, pp. 355-360, May 20, 1997.

Bucher, Heiner C., et al., "N-3 Polyunsaturated Fatty Acids in Coronary Heart Disease: A Meta-analysis of Randomized Controlled Trials", American Journal of Medicine, vol. 112, Mar. 2002, pp. 298-304.

Plat, J., et al., "Effects on serum lipids, lipoproteins and fat soluble antioxidant concentrations of consumption frequency of margarines and shortenings enriched with . . . ", European Journal of Clinical Nutrition, vol. 54, Apr. 17, 2000, pp. 671-677.

Matvienko, Oksana, A., et al., "A single daily dose of soybean phytosterols in ground beef decreases . . . " American Society for Clinical Nutrition, vol. 76, 2002, pp. 57-64.

Volpe, Roberto, et al., "Effects of yoghurt enriched with plant sterols on serum lipids in patients with moderate hypercholesterolaemia", British Jour. of Nutrition, 2001, vol. 86, pp. 233-239.

* cited by examiner

Figure 5

MULTI-VITAMIN AND MINERAL NUTRITIONAL SUPPLEMENTS

CROSS REFERENCE TO RELATED APPLICATION(S)

The present application is a continuation application of co-pending continuation U.S. patent application Ser. No. 13/023,671 filed Feb. 9, 2011, which is a continuation application of co-pending U.S. patent application Ser. No. 11/236,570 filed Sep. 28, 2005, which is a continuation-in-part application of U.S. patent application Ser. No. 11/090,486 filed Mar. 28, 2005, which claims priority from U.S. Provisional Patent Application No. 60/557,247, entitled "Multi-vitamin and Mineral Nutritional Supplements, the contents which are incorporated herein in their entirety to the extent that is consistent with this invention and application.

BACKGROUND OF THE INVENTION

This invention relates to nutritional supplements. Features of the invention include the provision in multi-vitamin and/or mineral supplements of ingredients and micro-nutrients to facilitate reduction of cholesterol, and/or reduction of homocysteine, and/or reduction of low-density lipoprotein-cholesterol (LDL-C) oxidation in humans. In particular, the invention relates to multi-vitamin and/or mineral supplements which include at least one component known to reduce cholesterol.

It has long been established that a number of chemical compounds typically referred to as vitamins and minerals provide significant value to maintaining an individual in a healthy state and/or treating specific medical conditions even when supplied in relatively small amounts. Over the years a number of such vitamins and minerals have been identified. For example, vitamins include A, C, D, E and the family of B vitamins and minerals include iron, zinc, calcium and chromium. The human body does not synthesize most of these compounds which are essential to maintaining the health of the human body. Thus these necessary vitamins and minerals must be obtained from an external source. The two most common external sources are foods and nutritional supplements. Food is typically the primary source of obtaining the necessary nutrients; however, the majority of people do not eat foods that consistently provide the necessary daily requirements of vitamins and minerals. Thus, vitamin and mineral nutritional supplementation has become a recognized method of meeting accepted medical and health standards.

While certain vitamins and minerals have been shown to be essential for maintaining an individual's health, the use of vitamin and mineral nutritional supplementation has afforded the possibility to include micro-nutrients which, although not absolutely essential to maintaining health, provide significant benefit towards maintaining health. For example, U.S. Pat. No. 6,361,800 to Cooper et al. provides for a multi-vitamin supplement preparation with a composition of micro-nutrients which is purported to decrease plasma homocysteine levels and plasma glucose levels.

A significant health concern to many individuals is the problem of high cholesterol. While many medications are available for treating this problem, most of the common medications require doctor's supervision for use and are relatively expensive. Certainly a doctor's care and use of these medications in cases of highly elevated or chronically elevated cholesterol are very important but the medications are used when the cholesterol level is a serious health threat.

Some herbal/natural vitamin and/or mineral and/or nutritional compositions that contain phytosterols, compounds which are believed to facilitate cholesterol reduction, are commercially available. However, the efficiency of these herbal/natural product compositions for reducing cholesterol is questionable as they typically contain 20 to 50 mg of phytosterol per dose. This is substantially below the amount that the FDA (Food and Drug Administration) recognizes as an efficacious dose of phytosterol for reducing cholesterol levels. In 21 CFR 101.83 dated Feb. 14, 2003, the FDA indicates that 800 mg/day is the lowest effective intake of the phytosterols to reduce risk of coronary heart disease.

Accordingly, it would be desirable to have a convenient, practical and relatively inexpensive way to facilitate reducing cholesterol levels, and/or reducing homocysteine, and/or decreasing LDL-C oxidation in humans before the cholesterol reaches a level to become a serious health threat.

SUMMARY OF THE INVENTION

The present invention provides a nutritional supplement which facilitates providing an adequate intake of vitamins, minerals and other micro-nutrients desirable for disease prevention, protection against nutritional losses and deficiencies due to inadequate dietary intake patterns and life style factors and provides micro-nutrients to facilitate reduction of cholesterol, and/or reduction of homocysteine, and/or reduction of LDL cholesterol in humans. The invention also provides a method of preparing an efficacious dosage of the nutritional supplement in a practical dosage form and a method for reducing cholesterol levels and/or LDL cholesterol and/or homocystine in humans.

In one embodiment the invention provides a nutritional supplement for administration to humans comprising: an effective amount of at least one vitamin selected from the group consisting of Vitamin A; Vitamin C; Vitamin E, Vitamin $B_6$, Vitamin $B_2$, folate and Vitamin $B_{12}$ and an effective amount of at least one cholesterol reducing agent selected from the group consisting of phytosterols, phytostanols, policosanols, and statins.

In one embodiment the invention provides a nutritional supplement for administration to humans comprising: an effective amount of at least one mineral selected from the group consisting of selenium, chromium and zinc, and an effective amount of at least brie cholesterol reducing agent selected from the group consisting of phytosterols, phytostanols, policosanols, and statins.

In one embodiment the invention provides a multi-vitamin and mineral nutritional supplement for administration to humans comprising at least one cholesterol reducing agent from the group consisting of phytosterols, phytostanols, policosanols and statins in an amount effective to reduce cholesterol and an effective of amount of vitamins A, $B_2$, $B_6$, $B_{12}$, folate (folic acid), and E. The composition may further comprise at least one of an effective amount of lycopene and an effective amount of selenium.

In another embodiment the invention provides a multi-vitamin and mineral nutritional supplement for administration to humans comprising pharmaceutically acceptable forms of the following: at least about 800 mg of phytosterols; at least about 3500 I.U. of vitamin A and/or vitamin A precursors; at least about 60 mg of vitamin C; at least about 400 I.U. of vitamin D; at least about 30 I.U. of vitamin E; at least about 25 mcg of vitamin K; about 1.5 mg of thiamin; at least about 1.7 mg of vitamin $B_2$ (riboflavin); at least about 20 mg of niacin; at least about 5 mg of vitamin $B_6$; at least about 800 mcg of folic acid; at least about 200 mcg of vitamin $B_{12}$; at least about 30 mcg of biotin; at least about 10 mg of pantothenic acid; at least about 6 mg of iron; about 150 mcg of iodine; at least about 210 mg of magnesium; at least about 7.5 mg of zinc; at least about 20 mcg of selenium; at least about 0.7 mg of copper; at least about 2 mg of manganese; at least about 108 mg calcium; at least about 80 mg of phosphorus; at least about 75 mcg of molybdenum; at least about 320 mcg boron; at least about 5 mcg nickel; at least about 2 mg silicon; at least about 10 mcg tin; at least about 10 mcg vanadium; at least about 120 mcg of chromium; at least about 64 mg of potassium; at least about 78 mg of chloride; at least about 300 mcg of lycopene; and at least about 250 mcg lutein.

Another embodiment of the invention provides a multi-vitamin and mineral nutritional supplement for administration to humans comprising pharmaceutically acceptable forms of the following: at least one ingredient to facilitate reduction of cholesterol, at least one ingredient to facilitate reduction of homocysteine or facilitate reduction of low-density lipoprotein-cholesterol (LDL-C) and about 1300 I.U. to about 10,000 I.U. of vitamin A and/or vitamin A precursors; about 200 I.U. to 2000 I.U. of vitamin D; about 0 mcg to about 50 mcg of vitamin K; about 1.2 mg to about 4.5 mg of thiamin; about 5 mg to about 40 mg of niacin; about 0 mg to about 550 mg of choline; about 0 mcg to about 1400 mcg of folic acid; about 0 mcg to about 300 mcg of biotin; about 0 mg to about 16 mg of pantothenic acid; about 0 mg to about 18 mg of iron; about 0 mcg to about 300 mcg of iodine; about 0 mg to about 100 mg of magnesium; about 3 mg to about 15 mg of zinc; about 0 mg to about 2 mg of copper; about 0 mg to about 6 mg of manganese; about 0 to about 200 mg calcium; about 0 mg to about 750 mg of phosphorus; about 0 mcg to about 250 mcg of molybdenum; about 0 mcg to about 150 mcg boron; about 0 mcg to about 100 mcg nickel; about 0 mg to about 40 mg silicon; about 0 mcg to about 35 mcg tin; about 0 mcg to about 25 mcg vanadium; about 0 mcg to about 300 mcg of chromium; about 0 mg to about 125 mg of potassium; about 0 mg to about 120 mg of chloride; about 0 to 3 g of Omega-3 fatty acids; about 0 to 3 g lycopene; about 0 to 3 g zeaxanthin; and about 0 mcg to about 3 g lutein.

Ingredients to facilitate reduction of cholesterol may comprise one or more of the following ingredients in an amount effective to reduce cholesterol: phytosterols, pliytostanols, or their equivalents, in free or esterified form, policosanol and statins. Suitable statins include, for example, atorvastatin, provastatin, simvastatin, lovastatin or flavastatin. Typically about 0.8 grams to about 3 grams of phytosterols, stanols, or their equivalents, may be used in the multi-vitamins and mineral nutritional supplements. Amounts of policosanol of up to about 200 mg may be used in the multi-vitamins and mineral nutritional supplements. Statins may be used in amounts of up to 80 mg and typically are used in amounts of about 40 mg to about 80 mg. More particularly with regard to statins, provastatin and simvastatin are preferably used in amounts of about 40 mg, and atorvastatin, lovastatin and fluvastatin are typically used in amounts of about 80 mg.

Ingredients to facilitate reduction of homocystine may comprise one or more of the following: up to about 40 mg of vitamin $B_2$ (riboflavin); up to about 10 mg of vitamin $B_6$; up to about 1 mg of folate, and up to about 2 mg of vitamin $B_{12}$. Ingredients to facilitate reduction of homocysteine, may more preferably comprise one or more of the following: about 1.3 mg to about 5.1 mg of vitamin $B_2$ (riboflavin); up to about 1400 about 800 mcg folate; about 1 mg to about 6 mg of vitamin $B_6$; and about 2.4 meg to about 200 mcg of vitamin $B_{12}$.

Ingredients to facilitate reduction of low-density lipoprotein-cholesterol cholesterol (LDL-C) oxidation, which may comprise one or more of the following: up to about 2 grams of vitamin C; up to about 800 I.U. of vitamin E; up to about 6 grams of lycopene; and up to about 350 mcg of selenium. Ingredients to facilitate reduction of low-density lipoprotein-cholesterol cholesterol (LDL-C) oxidation, may more preferably comprise one or more of the following: about 45 mg to about 250 mg of vitamin C; about 20 I.U. to about 200 I.U. of vitamin E; about 0 mcg to about 3 g of lycopene; and about 0 mcg to about 75 mcg of selenium.

The composition described herein may further include a diluent such as, for example a calcium compound, magnesium compound, microcrystalline cellulose, starch or a combination thereof.

The composition described herein may also include an absorbent such as silicon dioxide, for example. In some embodiments the silicon dioxide may be precipitated, fumed or a mixture thereof.

The invention further provides a method of reducing cholesterol levels, reducing homocysteine, and decreasing low-density lipoprotein-cholesterol (LDL-C) oxidation in humans by administering the composition of the invention to a human.

The invention further includes a method of tableting nutritional supplements comprising at least one phytosterol, the method comprising: providing at least one phytosterol and at least one diluent; granulating the phytosterol and the at least one diluent under high shear granulation conditions to form a granulation; milling the granulation; and adding an absorbent to the granulation.

For wet granulation methods, the method may further comprise drying the granulation and the absorbent is preferably added after drying. A fluid bed dryer is exemplary of a suitable dryer for drying the granulation.

The method may comprise compressing the granulation to form a tablet. The tableting may be coated with a film coat comprising polyvinyl alcohol (PVA), for example.

In one embodiment a daily efficacious amount of nutritional supplement comprises two tablets, each of the two tablets having a volume less than 2 cubic centimeters.

In one embodiment a daily efficacious amount of the nutritional supplement comprises four tablets or fewer. Each tablet having a volume less than 1.5 cubic centimeters.

In some embodiments the tablets may have an oblong, oval, modified oval, or capsule shape.

Alternatively a daily efficacious amount of the nutritional supplement may comprise one or more capsules, one or more chewable delivery unit, a powder, or a sachet.

DETAILED DESCRIPTION OF THE INVENTION

The invention provides a nutritional supplement which in one embodiment is a multi-vitamin and mineral nutritional supplement for administration to humans, having at least one ingredient to facilitate reduction of cholesterol. The cholesterol reducing ingredient may include phytosterols and/or stanols, and/or statins, and/or policosanol. In some embodiments the nutritional supplement further includes at least one ingredient for reduction of homocysteine and/or reduction of low-density lipoprotein-cholesterol (LDL-C). The multi-vitamin and mineral nutritional supplement may comprise one or more of: vitamin A and/or vitamin A precursors; vitamin C; vitamin D; vitamin E; vitamin K; thiamin; vitamin $B_2$ (riboflavin); niacin; vitamin $B_6$; folic acid; vitamin $B_{12}$; biotin; pantothenic acid; iron; iodine; magnesium; zinc; selenium; copper; manganese; calcium; phosphorus; molybdenum; boron; nickel; silicon; tin; vanadium; chromium; potassium; chloride; choline; lycopene; and lutein. When administered to a human on a regular basis (for example, daily), the composition of the invention facilitates adequate intake of vitamins and minerals and provision of other micro-nutrients to promote good health including micro-nutrients which facilitate the lowering of cholesterol levels, and/or reduction of homocysteine, and/or decrease of low-density lipoprotein-cholesterol (LDL-C) oxidation in humans. In other embodiments, the nutritional supplement may include one or more vitamins in combination with at least one cholesterol lowering ingredient, or at least one mineral in combination with at least one cholesterol-lowering ingredient. The terms "nutritional supplement" or "supplement" should be taken to refer to any or all of the embodiments (e.g. a multi-vitamin and mineral supplement with at least one cholesterol lowering agent, a composition comprising at least one vitamin and at least one cholesterol lowering agent, or a composition comprising at least one mineral and at least one cholesterol lowering agent). The nutritional supplement may in some embodiments further comprise other actives such as for example, homocystine lowering actives or one or more other actives that provide a nutritional and/or health benefit. A preferred embodiment of the invention is a multi-vitamin and mineral supplement with at least one cholesterol lowering agent, as such supplement provides a simple method for addressing nutritional deficiencies and promotes compliance in usage by an individual in need of nutritional supplementation.

The invention further provides a method for preparing solid dosages forms comprising nutritional supplement components in efficacious amounts in a unit or units compatible with convenient human consumption. (For example, in a dosage form in which a daily efficacious amount of at least one vitamin and/or mineral supplement and at least one cholesterol reducing ingredient is contained in 2-4 tablets of a size that an adult human can practically swallow.) Typically the number and amount of vitamin and mineral components needed to provide a efficacious daily dosage to generally supplement nutritional deficiencies constitutes a substantial tablet volume. Provision of an additional component(s) in the supplement to facilitate the reduction of cholesterol further increases the volume of material to be included in a dosage form.

Preparing a solid dosage form containing efficacious amounts of a significant number of vitamins and minerals and phytosterol in a practical dosage unit, for example, is particularly challenging in that a minimum of 800 mg of phytosterol per day is needed to meet the FDA standard for efficacy and phytosterol is a waxy material with a low bulk density. The inventors have addressed these problems by developing a preparation method (e.g. manufacturing process) that employs granulation techniques and/or the use of diluent and/or the use of absorbent excipients to prepare a tableted dosage form comprising efficacious daily amounts of the components of the nutritional supplement in preferably 2-4 tablets of a tablet size suitable to be swallowed by a human.

As used herein, the phrase "cholesterol lowering agent" or "cholesterol reducing agent" means any compound, combination of compounds, including any extract or plant component, naturally found or processed, or synthetic compound that has the property of lowering cholesterol levels when administered in an effective amount.

All amounts specified herein are based on milligrams unless otherwise indicated. The term "I.U." represents International Units. The term "mcg" means micrograms, "mg" means milligrams, and "g" means grams. Further, it should be understood that the amounts of components disclosed herein are for a daily dosage and that a daily dosage may comprise one dosage unit or a plurality of dosage units.

"An efficacious dosage" of a nutrient is at least the minimum amount of the nutrient needed on a daily basis recognized by the United States Food and Drug Administration (FDA) for providing a health or nutritional benefit. We further note that in some guidelines the FDA recommends that daily dosages of multivitamin and mineral supplements be divided and administered in two dosage units taken at spaced intervals during the day. Typically, with meals or food, for example such as twice daily with meals. Accordingly amounts are given for daily dosages but it should be understood that the daily dosage may be in multiple dosage units and consumption of these units may occur at the same time or different times during the day.

Typically, sterols and stanols derived from plant sources are termed phytosterols and phytostanols. Phytosterols and phytostanols are natural compounds that can be consumed regularly as a part of a healthy diet. Accordingly, while plant derived materials are the preferred source of these compounds, equivalent synthesized stanols and sterols, or stanols and sterols from other sources, may be used in the practice of the invention. Any reference to use of phytosterol or phytostanols herein should be taken to apply to equivalent sterols or stanols from alternative sources. It should be understood in terms of discussing amounts of the composition that sterols or phytosterols may be used in like amounts or vice-versa. It should be understood in terms of discussing amounts of the composition, that stanols or phytostanols may be used in like amount or vice-versa.

There are multiple specific chemical entities classed as phytosterols, including but not limited to beta-sitosterol, campesterol, and stigmasterol, for example. For the nutritional supplements of this invention either a single specific chemical species of phytosterol or mixtures comprised of a plurality of specific chemical species of phytosterols may be employed. For example, a mixture of phytosterols having beta-sitosterol, campesterol and sigmasterol as principle components is exemplary of a mixture suitable for use in the practice of the invention. Commercial preparations of mixed phytosterols are available from suppliers such as Cargill and ADM (Archer Daniels Midland), for example. Likewise, the class phytostanols includes multiple specific chemical species of phytostanols and a single specific chemical species of phytostanol or a mixture of a plurality of specific chemical species of phytostanols may be used in the practice of the invention. Accordingly, reference to phytosterols or phytostanols in compositions discussed herein should be taken to include both single specific chemical species forms as well as mixtures.

Foods such as fruits, vegetables, breads and other whole grain products, and most vegetable oils contain at least some phytosterols. However, it is difficult to consume enough of these foods on a daily basis to obtain sufficient phytosterol intake to have a cholesterol-lowering effect. Based on clinical trial data on the use of phytosterols in the diet, a daily intake of at least 0.8 grams (800 mg) of phytosterols as part of a diet low in saturated fat and cholesterol is recommended by the FDA to provide significant cholesterol lowering benefits. Consuming the nutritional supplements of this invention is one way to ensure that an effective daily intake is attained.

It is believed, but the inventors do not wish to be bound to the theory, that ingested plant sterols and stanols compete with the cholesterol to decrease cholesterol absorption and reabsorption in the small intestine because they are structurally similar to cholesterol. To a point, the more sterol, such as phytosterol, in free form that is present in the intestine following a meal, the less cholesterol absorption and reabsorption will occur. Further, consumed phytosterols, phytostanols, and their equivalents, are not absorbed to any appreciable extent. Hence, phytosterols are believed to inhibit the uptake of cholesterol by the body and are flushed through the system without absorption. One study showed that the overall effect may be an average decline in blood levels of "bad" low-density lipoprotein-cholesterol (e.g. the "LDL-C") of 8-15%, with no observed or identified adverse effects. (See "Plant Sterol-Fortified Orange Juice Effectively Lowers Cholesterol Levels In Mildly Hypercholesterolemic Healthy Individuals." Arterioscler. Thromb. Vase. Biol. 2004 March; 24(3):e25-8. Epub 2004 February 5) Preferably, the multi-vitamin and mineral nutritional supplement comprises up to about 3 g of the free form or the esteritied form of phytosterols and more preferably at least about 800 mg of phytosterols. Most preferably, the supplement comprises about 800 mg of phytosterols in the free form. In some embodiments the phytosterol may be replaced with phytostanols or a combination of phytosterols and phytostanols may be used.

Policosanol is the generic term used for a mixture of long-chain primary aliphatic saturated alcohols that may reduce total serum cholesterol and low-density lipoprotein-cholesterol (LDL-C) levels. Policosanol is also known as policosanol, policosanal, policosinal, policosinol, polycosanal, polycosinal and polycosinol. These alcohols are derived from the waxes of such plants as sugar cane (*Saccharum officinarium*) and yams (e.g. *Dioscorea opposita*). They are also found in beeswax. The main long-chain alcohol in policosanol is the 28 carbon 1-octanosol, and next most abundant is the 30 carbon 1-triacontanol. Other long-chain alcohols present in much lower concentrations comprise: 1-docosanol ($C_{22}$), 1-tetracosanol ($C_{24}$), 1-hexacosanol ($C_{26}$), 1-heptacosanol ($C_{27}$), 1-nonacosanol ($C_{29}$), 1-dotriacontanol ($C_{32}$) and 1-tetracontanol ($C_{34}$). These long-chain alcohols are solid waxy substances and are insoluble in water. They are known collectively as aliphatic alcohols.

The mechanism of action of reported cholesterol-lowering activity of policosanol is unknown and the inventors do not wish to be bound to any theory. Several theories regarding the method of action of policosanol have been suggested in the literature including the suggestion from some animal studies that policosanol may inhibit cholesterol synthesis in the liver by indirectly down-regulating HMG-CoA reductase. (see "Policosanol Safety Down Regulates HMG-CoA Reductase—Potential As A Component of the Esselstyn Regimen." Med. Hypotheses. 2002 September; 59(3):268-79.) Others have suggested Policosanol may impair cholesterol synthesis between the acetate and mevalonate production steps and/or increase receptor-dependent LDL-C processing. (see "Policosanol: Clinical Pharmacology and Therapeutic Significance of a New Lipid-Lowering Agent." Am. Heart J. 2002 February; 143(2): 356-65). Others have suggested Policosanol also may reduce lipid peroxidation (see "Effect of Policosanol on In Vitro and In Vivo Rat Liver Microsomal Lipid Peroxidation." Arch. Med. Res. 1997 Autumn; 28(3): 355-60). It is believed that the long-chain alcohols appear to have different biological activities, e.g. octacosanol by itself may not have the same activities as policosanol and that at least in some instances the combination of all or some of the alcohols in the policosanol may work synergistically. In one embodiment policosanol is included in the multivitamin and mineral nutritional supplement. The multi-vitamin and mineral nutritional supplement embodiment including policosanol comprises up to about 200 me of policosanol and more preferably about 10 to about 20 mg of policosanol.

Statins, including atorvastatin, pravastatin, simvastatin, lovastatin, and fluvastatin, are believed to be competitive 3-hydroxy-3 methyl glutaryl CoA, hereinafter referred to as EIMGCoA reductase inhibitors. Accordingly, they are believed to be effective in the reduction of cholesterol, and are believed to be effective in preventing not only recurrent heart attacks, but also first heart attacks. In some cases statins may also reduce the risk of strokes. In one embodiment statins may be included in the multi-vitamin and mineral nutritional supplement. The nutritional supplement embodiment including statins may comprise up to about 80 mg of a statin or mixture of statins and more preferably it comprises about 5 to about 80 mg of a statin or mixture of statins. Provastatin and simvastatin are preferably used in amounts of about 40 mg, and atorvastatin, lovastatin and fluvastatin are preferably used in amounts of about 80 mg.

Several vitamins and minerals are known to facilitate cholesterol reduction, homocysteine reduction, and/or reduction of low-density lipoprotein-cholesterol. By providing one of these agents, or a combination thereof, in a multi-vitamin and nutritional mineral supplement, this invention provides for a convenient, practical and relatively inexpensive way to facilitate reducing cholesterol levels, and/or reducing homocysteine levels, and/or decreasing LDL-C oxidation in humans.

Vitamin C, also known as ascorbic acid, is believed to be necessary for the synthesis of collagen and is used as an antioxidant. It is believed that Vitamin C fights infection, reduces inflammation, heals wounds, reduces the risk of heart disease by reduction of LDL-C oxidation, lowers cholesterol, reduces the risk of lung, stomach and esophageal cancers, reduces cervical epithelial abnormalities, inhibits N-nitrosamine, and reduces the severity of colds. The nutritional supplement may comprise up to about 2000 mg of Vitamin C, more preferably about 45 mg to about 250 mg, and most preferably about 60 mg of Vitamin C.

Vitamin E is needed for the maintenance of cell membranes and for neurological health. Vitamin E relieves hot flashes, relieves mastodynia, helps in fighting fibrocystic breast disease, reduces mammary tumors, reduces the risk of lung cancer, and reduces the risk of heart disease by reduction of LDL-C cholesterol oxidation. Vitamin E is the generic term for a group of related substances, which include alpha-tocopherol, beta-tocopherol, gamma-tocopherol, and delta-tocopherol. In addition, each of these four compounds has a "d" form, which is the natural form, and a "dl" form, which is the synthetic form. All forms of all substances covered by Vitamin E are included herein. The nutritional supplement may comprise up to about 1500 I.U. of Vitamin E, and more preferably about 15 I.U. to about 800 I.U. Most preferably, the multi-vitamin and mineral nutritional supplement may comprise about 20 I.U. to 200 I.U. of Vitamin E.

The nutritional supplement may comprise one or more of B complex vitamins. The B vitamins included in the nutritional supplement may include thiamin (Vitamin $B_1$), riboflavin (Vitamin $B_2$), niacin (Vitamin $B_3$) pantothenic acid (Vitamin $B_5$), pyridoxine (Vitamin $B_6$), biotin, folic acid, and the cobalamins (Vitamin $B_{12}$) or a combination thereof. The B vitamins are water-soluble. Of these vitamins, $B_2$, $B_{63}$ and Vitamin $B_{12}$ (e.g. or the cobalamins), are known to reduce homocysteine levels. However, because of the beneficial nature of the B vitamins in general, all of them are contemplated for use in one embodiment of the invention.

Vitamin $B_1$ or thiamin helps keep collagen-rich connective and mucous membranes healthy, helps to maintain smooth muscles, helps in the formation of blood cells, and is necessary for proper nervous system function. The nutritional supplement may comprise about 0.9 mg to about 100 mg of, more preferably about 1.2 mg to about 4.5 mg and most preferably about 1.5 mg of thiamin.

Vitamin $B_2$ or riboflavin is necessary for healthy hair, nails and mucous membranes and is involved in red blood cell formation, homocysteine reduction, antibody production and overall growth. The nutritional supplement of the invention may comprise up to about 40 mg of riboflavin, more preferably about 0.9 mg to about 5.1 mg and most preferably about 1.3 to 1.7 mg of riboflavin.

Vitamin $B_3$ or niacin helps in the production of most of the sex hormones, dilates blood vessels and helps maintain blood circulation. Niacin is the generic name for a group of compounds, which exhibit niacin activity and includes niacinamide and nicotinic acid. The nutritional supplement may comprise about 5 mg to about 500 rug of niacin, more preferably about 5 mg to about 40 mg and most preferably about 20 mg of niacin as niacinamide.

Vitamin $B_6$ or pyridoxine is involved in the production of ribonucleic acid (RNA) and deoxyribonucleic acid (DNA), homocysteine reduction, and many other reactions in the body. Pyridoxine refers to and includes three different compounds: pyridoxine, pyridoxamine, and pyridoxal. The nutritional supplement may comprise about 1 mg to about 10 mg of Vitamin $B_6$, more preferably about 1 mg to about 6 mg, and most preferably about 5 mg of Vitamin $B_6$.

Folic acid is used in the production of red blood cells, the production of hormones, and the synthesis of DNA. The nutritional supplement may comprise up to about 1000 mcg of folic acid, more preferably about 0 mcg to about 800 mcg folate (folic acid), and most preferably, about 800 meg of folic acid.

Vitamin $B_{12}$ (e.g. the cobalamins) is necessary for overall metabolism, the function of the nervous system, metabolism of folic acid, homocysteine reduction, and the production of red blood cells. There are at least three active forms of cobalamin: cyanocobalamin, hydroxocobalamin, and nitrocobalamin. The nutritional supplement may comprise up to about 2000 mcg of Vitamin $B_{12}$, more preferably about 2.4 meg to about 200 meg, and most preferably, about 200 mcg of Vitamin $B_{12}$.

Biotin is necessary for the metabolism of carbohydrates, proteins, and fats and is needed for healthy skin and hair. The nutritional supplement may comprise up to about 900 mcg of biotin and more preferably about 0 mcg to about 300 meg, and most preferably, about 30 mcg of biotin.

Pantothenic acid, also known as Vitamin $B_5$, is important for the production of adrenal gland hormones, increases overall energy, and helps convert food into energy. The nutritional supplement may comprise up to about 200 mg of pantothenic acid, more preferably about 0 mg to about 10 mg, and most preferably, about 10 mg of pantothenic acid.

Vitamin A is also contemplated for use in the multi-vitamin and mineral nutritional supplement of the invention. Vitamin A prevents night blindness and other eye disorders, keeps skin moist and elastic, maintains healthy hair, skin, and gums, reduces the risk of breast cancer, helps alleviate mastodynia, reduces the risk of lung cancer, maintains cell structure and integrity, works as an antioxidant to prevent cell aging, helps prevent infection, and negates skin wrinkling and the effects of sun damage. Vitamin A is a fat-soluble vitamin. The term Vitamin A is used to include retinol and other chemically similar compounds referred to as retinoids.

In the practice of the invention, Vitamin A may be provided as a form of Vitamin A, as Vitamin A precursor carotenoids, such as hetacarotene, or as a mixture thereof. For example, in a typical embodiment 29% of Vitamin A may be provided as beta-carotene, with the remainder supplied as Vitamin A acetate. The nutritional supplement of the invention may comprise up to about 10,000 I.U. of Vitamin A including Vitamin A precursors, more preferably about 1300 I.U. to about 5000 I.U. and most preferably, about 3500 I.U. of Vitamin A in the form of Vitamin A or Vitamin A and the Vitamin A precursor beta-carotene.

Beta-carotene and other carotenoids are provitamins, i.e., vitamin precursors, and are converted to vitamins or vitamin-like substances, as the body requires. Although the carotenoids include lutein, zeaxanthin and lycopene, amounts of these components are specified specifically herein and any amounts of Vitamin A precursors recited herein should not be interpreted to include any appreciable amount of lutein, zeaxanthin or lycopene.

Vitamin D is also an essential mineral which assists in the mineralization and calcification of bone, prevents rickets in children, prevents osteomalacia in adults, preserves bone and tooth growth, and lowers blood pressure. Vitamin D is fat-soluble and cholecalciferol or $D_3$ is the preferred form. Preferably, the nutritional supplement may comprise up to about 2000 I.U. of Vitamin D and more preferably about 200 to about 400 I.U. of Vitamin D.

Vitamin K is an active blood clotting agent and assists in bone formation. It also may help in removing calcium from atherosclerotic plaques. Phylloquinone or K1 and menoquinone, or K2 are the preferred forms. Preferably, the nutritional supplement may comprise up to about 1 mg of vitamin K, more preferably about 0 mcg to about 90 mcg of vitamin K and most preferably about 25 meg vitamin K.

Choline is necessary for nervous system function and brain function. It is also important for gall bladder and liver function. Choline helps maintain the structural integrity of membranes surrounding every cell in the body but also can play a role in nerve signaling, cholesterol transport, and energy metabolism. In the nutritional supplement, choline may be provided in the form of a pharmaceutically acceptable choline salt, such as, for example, bitartarate. The nutritional supplement may optionally comprise of up to about 3500 mg choline, and more preferably, of about 50 mg to about 550 mg of choline in the form of choline bitartarate.

Iron is used in the production of hemoglobin and myoglobin. In the nutritional supplement, the iron is dosed in the form of a pharmaceutically acceptable iron compound. As used herein, "pharmaceutically acceptable" is a component which is suitable for use in humans without undue side effects, such as irritation, toxicity, and allergic response. Useful pharmaceutically acceptable iron compounds include, but are not limited to, ferrous fumarate, ferrous sulfate, carbonyl iron, ferrous gluconate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes, and combinations thereof. The nutritional supplement may comprise up to about 18 mg of iron dosed in a pharmaceutically acceptable iron compound and more preferably, about 5 mg to about 18 mg of iron.

Iodine helps to metabolize fats, is necessary for proper thyroid function, and reduces fibrocystic breast conditions. In the nutritional supplement of the invention, iodine is dosed in the form of a pharmaceutically acceptable iodine compound. Useful pharmaceutically acceptable iodine compounds include, but are not limited to, potassium iodide, sodium iodide and combinations thereof. The nutritional supplement may comprise up to about 1100 mcg of iodine dosed in the form of a pharmaceutically acceptable iodine compound, more preferably up to about 150 mcg, and—most preferably, about 150 mcg of iodine.

Magnesium is used in bone formation and growth, prevents bone loss, relaxes coronary arteries, is used in managing pre-eclampsia, treating cardiac arrhythmias, and managing diabetes. In the nutritional supplement, magnesium is dosed in the form of a pharmaceutically acceptable magnesium compound. Useful pharmaceutically acceptable magnesium compounds include, but are not limited to, magnesium stearate, magnesium carbonate, magnesium oxide, magnesium hydroxide, magnesium sulfate, and combinations thereof. The nutritional supplement may comprise up to about 400 mg of magnesium dosed in the form of a pharmaceutically acceptable magnesium compound, more preferably up to about 350 mg, and most preferably, about 100 mg of magnesium.

Zinc is required for proper formation of DNA and RNA and is needed for growth, immunity and sexual development of women. In the multi-vitamin and mineral nutritional supplement of the invention, zinc is dosed in the form of a pharmaceutically acceptable zinc compound. Pharmaceutically acceptable zinc compounds include, but are not limited to, zinc sulfate, zinc chloride, zinc oxide, and combinations thereof. The nutritional supplement may comprise about 3 mg to about 40 mg of zinc dosed in the form of a pharmaceutically acceptable zinc compound, more preferably about 3 mg to about 15 mg and most preferably, about 15 mg of zinc.

Selenium reduces the risk of heart attacks and heart disease, reduces the risk of cancer, protects against metal poisoning, and is believed to be synergistic with Vitamin E in reducing LDL cholesterol oxidation. Pharmaceutically acceptable selenium compounds include but are not limited to sodium selenate, selenocysteine, selenomethionine or other amino acid chelates, and combinations thereof. The nutritional supplement may comprise up to about 400 mcg of selenium more preferably up to about 75 mcg and most preferably about 15 mcg to about 75 mcg of selenium dosed in a pharmaceutically acceptable form.

Copper helps keep blood vessels elastic, is needed for the formation of elastin and collagen, functions as an iron oxidizer, and is needed for the proper functioning of Vitamin C. In the nutritional supplement, copper is dosed in a pharmaceutically acceptable copper compound. Pharmaceutically acceptable copper compounds include, but are not limited to, cupric oxide, cupric citrate, cupric sulfate, cupric carbonate, cupric gluconate, and combinations thereof. The nutritional supplement may comprise up to about 10 mg of copper dosed in the form of a pharmaceutically acceptable copper compound, and more preferably, about 1.0 mg of copper dosed in the form of cupric gluconate, sulfate or citrate.

Calcium is needed by the body to build and maintain strong bones and teeth, facilitate neural transmission, and regulate muscle contraction and heartbeat. Calcium is lost through shed skin, nails, hair sweat, urine and feces. If intake is not sufficient, the body may remove calcium from bone to obtain the mineral which may adversely affect the bone density and render bones more susceptible to injury. Pharmaceutically acceptable calcium compounds include, but are not limited to, calcium carbonate, dibasic calcium phosphate, tribasic calcium phosphate, calcium gluconate, calcium lactate, calcium citrate, and combinations thereof. The nutritional supplement may comprise up to about 1500 mg calcium, more preferably up to about 200 mg and most preferably about 100 mg to about 162 mg of calcium dosed in a pharmaceutically acceptable form.

A low level of manganese in the body may be associated with diabetes. Accordingly manganese appears to have a role in the control of blood sugar levels. Manganese may also have a role in the metabolism of amino acids and certain vitamins. Pharmaceutically acceptable manganese compounds include, but are not limited to, manganese chloride, manganese sulfate, and combinations thereof. The nutritional supplement may comprise up to about 12 mg manganese dosed in a pharmaceutically acceptable form more preferably the nutritional supplement may comprise about 0 mg to about 4 mg manganese and most preferably about 1 mg manganese.

Silicon is believed to be used for the building of collagen for bones and connective tissue. Pharmaceutically acceptable silicone compounds include, but are not limited to, sodium silicate, sodium silicoaluminate, silicon dioxide, and combinations thereof. The nutritional supplement may comprise about 0 mg to about 500 mg silicon dosed in a pharmaceutically acceptable form, more preferably about 0 mg to about 60 mg silicon, and most preferably about 2 mg silicon.

Molybdenum may facilitate proper metabolism of fats, carbohydrate and iron and may protect against certain cancers. Pharmaceutically acceptable molybdenum compounds include, but are not limited to, sodium molybdate, molybdenum amino acid chelates, and combinations thereof. The nutritional supplement may comprise up to about 2000 mcg molybdenum dosed in a pharmaceutically acceptable form. More preferably the nutritional supplement may comprise about 0 mcg to about 75 mcg, and most preferably the nutritional supplement comprises about 75 mcg molybdenum.

Vanadium is believed to have a role in the regulation of sugar levels in the blood. Pharmaceutically acceptable vanadium compounds include, but are not limited to, ammonium vanadium tartrate, sodium metavanadate, vanadyl sulfate, and combinations thereof. The nutritional supplement may comprise up to about 1.8 mg vanadium in a pharmaceutically acceptable form, more preferably about 6 mcg to about 18 mcg vanadium and most preferably about 10 mcg vanadium.

Boron may have a role in mineral metabolism. Pharmaceutically acceptable boron compounds include, but are not limited to, sodium borate, boron citrate, boron amino acid chelates, and combinations thereof. The nutritional supplement may comprise up to about 20 mg of boron dosed in a pharmaceutically acceptable form, more preferably about 0 mcg to about 1.35 mg boron, and most preferably about 150 mcg to about 350 mcg boron.

Nickel may activate or inhibit the action of some enzymes or hormones. Pharmaceutically acceptable nickel compounds include, but are not limited to, nickel sulphate. The nutritional supplement may comprise up to about 1.0 mg nickel dosed in a pharmaceutically acceptable form, more preferably about 0 mcg to about 100 mcg nickel and most preferably about 5 mcg nickel.

Tin is known to be found in the human body. In rats a tin deficiency may depress growth. Pharmaceutically acceptable tin compounds include, but are not limited to, stannous chloride. The nutritional supplement may comprise up to about 200 mcg tin dosed in a pharmaceutically acceptable form, more preferably about 0 mcg to about 10 mcg tin and most preferably about 10 mcg tin.

Phosphorus is needed for bone development and is a constituent in all major classes of biochemical compounds. Phosphorous, in the form of phosphate in adenosine triphosphate is a key energy source required for most metabolic processes. Pharmaceutically acceptable phosphorus compounds include, but are not limited to, forms of calcium phosphate, sodium phosphate, potassium phosphate, ammonium phophate, glycerol phosphate, and combinations thereof. The nutritional supplement may comprise up to about 1250 mg of phosphorus, more preferably about 0 mg to 750 mg, most preferably about 109 mg of phosphorous, dosed in a pharmaceutically acceptable form.

Chromium assists in the regulation of glucose metabolism, is used in the synthesis of fatty acids and cholesterol, assists in transporting proteins, lowers LDL blood levels, and raises high density lipoproteins blood levels. In the nutritional supplement, chromium is dosed in a pharmaceutically acceptable chromium compound. Useful pharmaceutically acceptable chromium compounds include, but are not limited to, chromium chloride, yeast-bound chromium, picolinate, niacin-bound chromium, and combinations thereof. The nutritional supplement may comprise up to about 10 mg of chromium dosed in a pharmaceutically acceptable form, more preferably about 0 mcg to about 150 mcg chromium, and most preferably about 120 mcg of chromium.

Potassium is needed to regulate water balance, levels of acidity, blood pressure and neuromuscular function. Potassium is also required for carbohydrate and protein metabolism. In the nutritional supplement, potassium is dosed in the form of a pharmaceutically acceptable potassium compound. Useful pharmaceutically acceptable potassium compounds include, but are not limited to, potassium chloride, potassium sulfate; potassium glycerophosphate, potassium citrate, potassium gluconate, potassium phosphate, and combinations thereof. The nutritional supplement may comprise up to about 3900 mg of potassium dosed in a pharmaceutically acceptable form of potassium compound, more preferably about 0 mg to about 80 mg potassium, and most preferably about 50 mg to about 80 mg of potassium.

Lycopene has been found to reduce the risk of cancer and it has also been found to decrease LDL cholesterol oxidation via its antioxidant capabilities. Lycopene is found primarily in tomatoes, red grapefruit, watermelon, and other sources, and is a carotenoid. The nutritional supplement may comprise up to about 6 g lycopene, more preferably about 0 mcg to about 3 g lycopene and most preferably about 300 mcg lycopene.

Lutein and zeaxanthin are carotenoid antioxidants that help to maintain healthy eyesight, and have been found to reduce the risk of cancer and heart disease. Lutein has been found to decrease the risk and prevent the progression of macular degeneration, the leading cause of blindness in those over the age of 65. Lutein and zeaxanthin are primarily found in yellow corn, egg yolk, spinach, broccoli and other green leafy vegetables. The nutritional supplement may comprise up to about 6 g lutein in a pharmaceutically acceptable form, more preferably about 0 mcg to about 3 g lutein and most preferably about 250 mcg lutein. The nutritional supplement may comprise up to about 6 g zeaxanthin in a pharmaceutically acceptable form, more preferably about 0 mcg to about 3 g zeaxanthin and most preferably about 300 mcg zeaxanthin.

Epidemiological and intervention trials have demonstrated a cardio-vascular benefit from increased levels of Omega-3 fatty acids. In a recent (2002) meta-analysis Bucher et al. looked at the beneficial effects of Omega-3 fatty acids in randomized controlled trials. This analysis included 11 trials with 7951 patients. Bucher et al. "N-3 Polyunsaturated Fatty Acids in Coronary Heart Disearch: A meta-Analysis of Randomized Control Trials;" Am. J. Med.; March 2002, 112(4): pp 298-304. The trials included both dietary and supplement sources of Omega-3 fatty acids. They confirmed a statistically significant 30% reduction in the rate of sudden cardiac death in the population with increased Omega-3 fatty acid intakes from both diet and supplement sources. Preferably the nutritional supplement comprises up to about 6 g of Omega-3 fatty acids, more preferably about 0 g to about 3 g and most preferably about 1 g of Omega-3 fatty acids.

Chloride is needed to help maintain the ionic and fluid balance in the body, and is an essential component of gastric and intestinal secretions. Useful pharmaceutically acceptable chloride compounds include, but are not limited to, sodium chloride, chromium chloride, stannous chloride and potassium chloride. The multi-vitamin and mineral nutritional supplement preferably comprises up to about 100 mg chloride, more preferably about 0 mg to about 80 mg and most preferably about 50 mg to about 75 mg chloride.

The multi-vitamin and mineral nutritional supplement of the invention is intended for oral administration and may be provided in a solid form. In addition to the active material, the multi-vitamin and mineral nutritional supplement may further comprise excipients and processing aides such as: absorbents, diluents, flavorants, colorants, stabilizers, fillers, binders, disintegrants, lubricants, wetting agents, glidants, antiadherents, sugar or film coating agents, preservatives, buffer, artificial sweeteners, natural sweeteners, dispersants, thickeners, solubilizing agents and the like or some combination thereof.

The dosage forms of the present invention are typically considered to be solid. However, they may contain liquid or semi-solid components. Suitable "solid dosage forms of the present invention includes, but are not limited to, tablets, caplets, capsules including soft gel capsules, chewable dosage forms of and sachets and the like. The daily dosage may be included in a single delivery unit or may comprise multiple delivery units. Dividing the daily dosage among multiple delivery units may be desirable if a tablet is used, for example, to provide a tablet size that is convenient to swallow. If multiple delivery units are used, they may be administered at one time or administered at intervals during the dosage period (e.g. typically a day) if desired. Present FDA guidelines recommend that the daily dosage be divided and administered in two dosage units taken at spaced intervals. However, we note that at least three current clinical studies indicate that once daily dosing of phytosterols is efficacious. (See Plat J, et al. Effects On Serum Lipids, Lipoproteins and Fat Soluble Antioxidant Concentrations of Consuption Frequency of Margarines and Shortenings Enriched With Plant Sterol Esters. Eur J Clin Nutr 2000, 54:671-677; Matvienko O A et al. A Single Daily Dose of Soybean Phytosterols in Ground Beef Decreases Serum Total Cholesterol and LDL Cholesterol in Young Mildly Hypercholesterolemeic Men. Am J Clin Nutr 2002, 76:57-64; and Volpe, R. et al. Effects of Yogurt Enriched With Plant Sterols on Serum Lipids in Patients With Moderate Hypercholesterolemia. British Journal of Nutrition. 2001; 86:233-39.)

Accordingly it should be understood that the amounts of the vitamins, minerals and cholesterol reducing agents disclosed herein are for a daily dosage and that dosage may be delivered in a single delivery unit or multiple delivery units. In some embodiments packaging design may be used to facilitate identification of the proper daily dosage to the consumer. For example, a blister pack with labeling to indicate a daily dosage may be used.

Tableting compositions containing sterols such as phytosterol presents challenges. Phytosterol has a waxy nature, is hydrophobic, typically does not flow well in micronized form and has a low bulk density. These properties cause problems during the tablet making (tableting) process, which include, but are not limited to picking and sticking of materials to tooling, materials sticking to the press turntable during compression and poor tablet weight control. Further, phytosterol is difficult to mill because it tends to clog the mill screen unless cryo-milled. Prior to the present invention tablets high in phytosterol typically exhibited poor compressibility and once compressed had slow tablet disintegration adversely impacting delivery of the phytosterol upon ingestion. Timely disintegration is believed to be important for efficacy. As inventors believe, without wishing to be held to any theory, phytosterol acts in primary particle form in the gastrointestinal lumen.

The inventors have surprisingly discovered that use of certain granulating methods can yield a tablet containing at least one half the daily efficacious dose of phytosterol and at least one other vitamin or mineral in a single tablet which is a size that may be swallowed by a human. Further, the tablet of the invention disintegrates into primary particles in a time consistent with gastric emptying time, e.g. the compacted phytosterol containing tablet of the invention is believed to substantially disintegrate before reaching the gastrointestinal lumen. In one embodiment at least one half the daily efficacious dose of phytosterol and at least one half the daily efficacious dose of a plurality of vitamins and minerals are tableted in a single tablet that may be swallowed by a human and which disintegrates in time consistent with gastric emptying. In an embodiment in which a daily efficacious dose of the nutritional supplement is contained in two tablets it is preferable that the volume of each tablet is less than about 2 cubic centimeters.

In another embodiment an efficacious daily dose of the nutritional supplement of the invention is tableted in four tablets or less each of a size that can be swallowed by a human. Preferably when a daily efficacious dosage is contained in three or four tablets each tablet has a volume of about 1.5 cubic centimeters or less.

Figure 1:
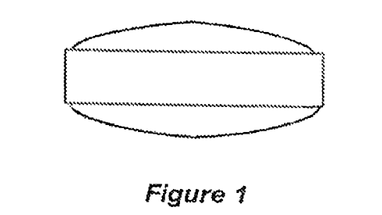
FIG. 1 is an end view of an exemplary embodiment of a tablet of the composition of the invention.
Figure 2:
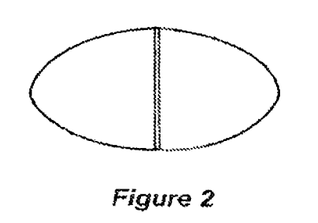
FIG. 2 is a top view of an exemplary embodiment of a tablet of the composition of the invention.
Figure 3:
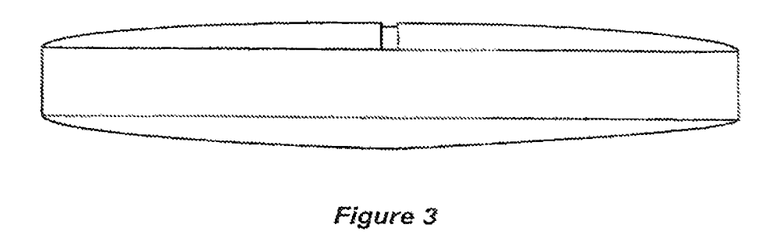
FIG. 3 is a side view of an exemplary embodiment of a table of the composition of the invention.

Tablet shape of a nutritional supplement is believed to contribute to several factors that may improve user compliance. The inventors believe, without being held to the theory, that oblong, oval, modified oval, and capsule shaped compacts of about 1.5 cubic centimeters in volume or less, for example are easier for a consumer to swallow than, for example, round compacts of about 1.5 cubic centimeters or less, for example. In some instances tablets that are easier to swallow may improve user compliance with the dosing regimen. FIGS. 1 to 3 show an exemplary embodiment of a tablet shape. As one skilled in the art will appreciate this shape is exemplary and any of many other shapes may be equally suitable in the practice of the invention.

In one embodiment, tablets may be prepared using a high shear wet-granulation method. In an exemplary high shear wet granulation method phytosterol is granulated with at least one diluent. The diluent may comprise one or more of the inorganic mineral nutrients described herein, such as, for example, a magnesium compound, or calcium compound, other active agents; inactive diluents such as, for example celluloses, cellulose derivatives, lactose or other sugars, polyols, starches, starch derivatives, polymers or mixture thereof. Utilizing one or more of the inorganic mineral nutrients as the diluent or a portion of the diluent has the advantage of minimizing added excipients and facilitates forming a smaller tablet. Dibasic calcium phosphate, and magnesium oxide are exemplary of specific magnesium and calcium compounds which both act as a nutrient and are useful as diluents. These diluents are exemplary and other diluents and granulation components or mixtures thereof known to those skilled in the art may be used for the granulation. Other granulation excipients known to those skilled in the art may be added such as povidone, disintegrants, co-disintegrants, super-disintegrants, surfactants, glidants, lubricants and binders. Further, other actives such as low dose mineral actives may be included in the granulation mixture. Inclusion of other low dose activities in the granulation may contribute only modestly to the granulation properties but addition to the granulation mixture facilitates uniform distribution of these low dose actives. In one exemplary embodiment the mixture subjected to granulation comprised the phytosterol, diluents, the binder polyvinyl pyrrolidone (PVP), the excipient crosprovidone, and water. The water was added slowly to the remaining ingredients while they were mixed in a high-shear granulator.

Optionally the granulation may be dried. The drying may be performed in a fluid bed dryer, for example. The granulation is milled to a suitable particle size. In one exemplarily embodiment a 0.05 screen was used. However, as one skilled in the art will appreciate this is exemplary and other sizes may be employed. After milling, the milled granulation is mixed with an absorbent. Silicon dioxide is exemplary of a suitable absorbent. Other materials known to these skilled in the art as absorbents may also be used in the practice of the invention.

Other vitamins, minerals and cholesterol reducing agent may be blended into the milled granulation with an absorbent preferably in an ordered blending after a portion of the absorbent is combined with the granulation. These additional components may be added as single ingredients, preformed mixes or a combination thereof. Other excipients such as flavorants, colorants, stabilizers, fillers, binders, disintegrants, lubricants, milling agents, glidants, antiadherents, preservatives, buffers, sweeteners, dispersants, thickness, solubilizing agent and the like or combination thereof may optionally be included.

After blending the composition may be formed into tablets using compression methods, for example. Optionally the tablets may be coated using tablet coating materials and methods such as those known to those skilled in the art. The waxy nature of the phyto sterols has been discovered to make adherence of a film-coating material to the tablet core difficult. The inventors have discovered that satisfactory adherence may be obtained using an aqueous based film-coating system comprising polyvinyl alcohol. Further, the inventors believe without wishing to be held to the theory, that using a film-coating comprising polyvinyl alcohol may improve patient compliance by yielding a tablet that is easier to swallow.

The inventors believe without wishing to be bound to the theory that their discovery of ordered blending of the phytosterol granulation with absorbent to coat or partially coat the granules facilitates disintegration of the tablet. Thus the inventors' discovery addresses the problem that untreated waxy phytosterols tend to form compacts with long disintegration times which are undesirable. The untreated compact compounds likely pass through the gastrointestinal track with minimum, if any, disintegration to primary particles which are believed to be necessary for efficacy.

The inventors further believe that the physical nature and size of the absorbent particle may modify the disintegration rate of the tablet. For example, the inventors have discovered that when the absorbent silicon dioxide was used at a 1:8 w/w ratio with phytosterols, slower disintegration was seen with a fumed silicon dioxide of about 0.2-0.3 micron particle size and about 200 meter squared per gram surface area than with a precipitated silicon dioxide of about 7 micron particle size and about 300 meter squared per gram surface area. The inventors believe that it is preferable to use precipitated silicon dioxide as described above as the absorbent for an immediate release phytosterol nutritional supplement and that a fumed silicon dioxide as described above as the absorbent may be used to modulate disintegration rate. As the physical nature and size of the absorbent appear to impact the rate of disintegration in some embodiments it may be desirable to use a mixture of absorbent types and/or particle size to facilitate obtaining the desired disintegration profile. Although silicon dioxide is referred to as an absorbent herein, the inventors note that the silicon dioxide may also function as an adsorbent (e.g. it may be a sorbent). For the purposes of this disclosure the distinction between absorbent and adsorbent is not critical and reference to absorbent should be taken to include absorbent, adsorbent, sorbents or combination thereof.

Figure 4:
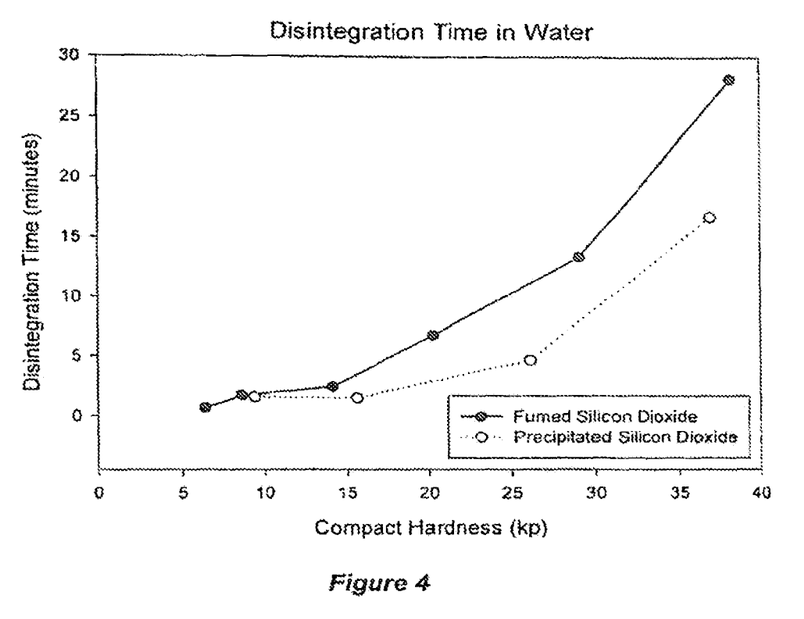
FIG. 4 is a graph showing tablet disintegration data for tablets of two exemplary embodiments of the composition of the invention in water.
Figure 5:
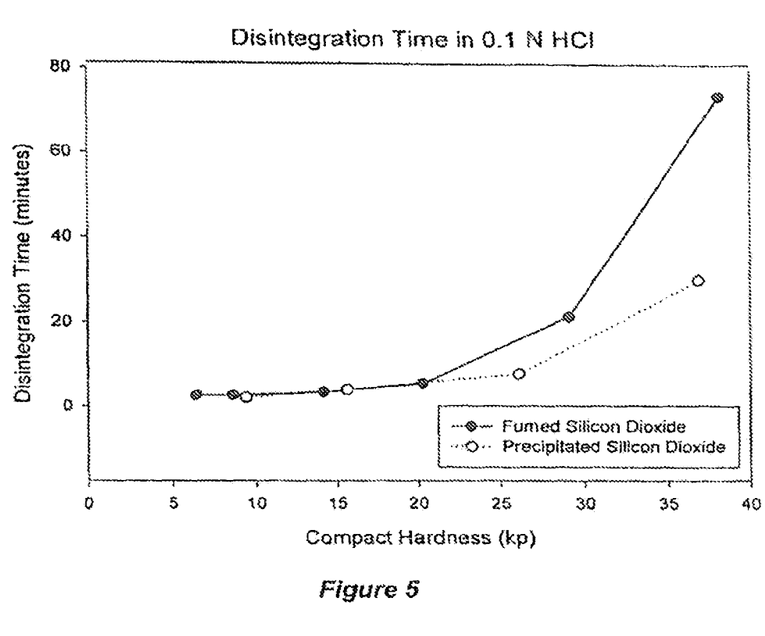
FIG. 5 is a graph showing tablet disintegration data for tablets of two exemplary embodiments of the invention in acid.

FIGS. 4 and 5 show exemplary disintegration date for two examples of the composition of the invention in water and acid, respectively. All examples in FIGS. 4 and 5 have disintegration times compatible with the timely disintegration in the gastrointestinal track. However, times do vary depending on the form of silicon dioxide used as FIGS. 4 and 5 show.

The high shear granulation method described herein is exemplary of a suitable method for preparing the composition of the invention. The inventors' also note that the wet granulation method described herein does not require expensive cryo-milling. Alternatively, methods such as dry slugging, dry roller compaction or extrusion could be used to prepare the compositions of the invention.

Optionally the nutritional supplement may be provided in a liquid and/or semisolid preparation. In addition to the active material such liquid and/or semisolid preparations may include excipients and processing aides such as: flavorants, colorants, stabilizers, buffers, artificial sweeteners, natural sweeteners, sequestering and/or chelating agents, dispersants, thickeners, solubilizing agents, humectants, antioxidants, emulsifiers, water, ethanol, glycerin, propylene glycol and the like or same combination thereof. The quantity of active material in a unit dose of the multi-vitamin preparation is varied according to the particular application and potency of the active ingredients.

Determination of the proper dosage for a particular situation is within the skill of the art. Optionally, the multi-vitamin and mineral nutritional supplement may be presented in a controlled release formulation.

Although the composition of the invention is preferably intended for administration to humans it should be understood that the formulation may also be utilized in veterinary applications for animals.

EXAMPLE 1

Multi-Vitamin and Mineral Nutritional Supplement

The composition of an exemplary embodiment of the invention is provided in Table 1. This composition is representative and is one of many compositions that are within the scope of the invention and is provided for illustrative purposes. The multi-vitamin and mineral nutritional supplement exemplified in Example 1 is intended to be a daily dosage and typically would be administered in one or more dosage units (e.g. one to four tablets). If multiple dosage units are used they may be taken at one time or spaced intervals during the day.

TABLE 1

| Ingredient | Amount/Day |
| --- | --- |
| Zinc | 7.5 mg |
| Vitamin K | 25 mcg |
| Vitamin E | 100 IU |
| Vitamin D | 400 IU |
| Vitamin C | 60 mg |
| Vitamin $B_6$ | 5 mg |
| Vitamin $B_2$ (riboflavin) | 1.7 mg |
| Vitamin $B_{12}$ | 200 mcg |
| Vitamin A (and Vitamin A precursors) | 3500 IU |
| Vanadium | 10 mcg |
| Tin | 10 mcg |
| Thiamin | 1.5 mg |
| Silicon | 2 mg |
| Selenium | 40 mcg |
| Potassium | 80 mg |
| Phytosterols | 800 mg |
| Phosphorous | 109 mg |
| Pantothenic Acid | 10 mg |
| Nickel | 5 mcg |
| Niacin | 20 mg |
| Molybdenum | 75 mcg |
| Manganese | 2 mg |
| Magnesium | 100 mg |
| Lycopene | 300 mcg |
| Lutein | 250 mcg |
| Iron | 6 mg |
| Iodine | 150 mcg |
| Folic Acid | 800 mcg |
| Copper | 0.7 mg |
| Chromium | 120 mcg |
| Chloride | 72 mg |
| Calcium | 162 mg |
| Boron | 150 mcg |
| Biotin | 30 mcg |

EXAMPLE 2

Multi-Vitamin and Mineral Nutritional Supplement

The composition of another exemplary embodiment of the invention is provided in Table 2. This is another composition representative of the composition within the scope of the invention and is provided for illustrative purposes. The multi-vitamin and mineral nutritional supplement of Example 2 is intended to be a daily dosage and typically would be administered in one or more dosage units (e.g. one to four tablets). If multiple dosage units are used they may be taken at one time or at spaced intervals during the day.

TABLE 2

| Ingredient | Amount/Day |
| --- | --- |
| Zinc | 7.5 mg |
| Zeaxanthin | 300 mcg |
| Vitamin K | 25 mcg |
| Vitamin E | 45 IU |
| Vitamin D | 400 IU |
| Vitamin C | 90 mg |
| Vitamin $B_6$ | 3 mg |
| Vitamin $B_2$ (riboflavin) | 1.7 mg |
| Vitamin $B_{12}$ | 25 mg |
| Vitamin A (and Vitamin A precursors) | 3500 IU |
| Vanadium | 10 mcg |
| Thiamin | 1.5 mg |
| Silicon | 2 mg |
| Selenium | 55 mg |
| Potassium | 80 mcg |

TABLE 2-continued

| Ingredient | Amount/Day |
| --- | --- |
| Phytosterols | 800 mg |
| Phosphorous | 100 mg |
| Pantothenic Acid | 10 mg |
| Nickel | 5 mcg |
| Niacin | 16 mg |
| Molybdenum | 45 mcg |
| Manganese | 2.3 mg |
| Magnesium | 100 mg |
| Lycopene | 600 mcg |
| Lutein | 500 mcg |
| Iodine | 150 mcg |
| Folic Acid | 600 mcg |
| Copper | 0.7 mg |
| Chromium | 50 mcg |
| Choline | 55 mg |
| Chloride | 72 mg |
| Calcium | 200 mg |
| Boron | 150 mcg |
| Biotin | 30 mcg |

EXAMPLE 3

Multi-Vitamin and Mineral Nutritional Supplement

The composition of another exemplary embodiment of the invention is provided in Table 3. This is another composition representative of the composition within the scope of the invention and is provided for illustrative purposes. The multi-vitamin and mineral nutritional supplement of Example 3 is intended to be a daily dosage and typically would be administered in one or more dosage units (e.g. one to four tablets). If multiple dosage units are used they may be taken at one time or at spaced intervals during the day.

TABLE 3

| Ingredient | Amount/Day |
| --- | --- |
| Zinc | 7.5 mg |
| Vitamin K | 25 mcg |
| Vitamin E | 30 IU |
| Vitamin D | 400 IU |
| Vitamin C | 60 mg |
| Vitamin $B_6$ | 5.0 mg |
| Vitamin $B_2$ (riboflavin) | 1.7 mg |
| Vitamin $B_{12}$ | 20 mcg |
| Vitamin A (and Vitamin A precursors) | 3500 IU |
| Vanadium | 10 mcg |
| Thiamin | 1.5 mg |
| Silicon | 2 mg |
| Selenium | 20 mcg |
| Potassium | 64 mg |
| Phytosterols | 800 mg |
| Phosphorous | 80 mg |
| Pantothenic Acid | 10 mg |
| Nickel | 5 mcg |
| Niacin | 20 mg |
| Molybdenum | 75 mcg |
| Manganese | 2.0 mg |
| Magnesium | 40 mg |
| Lycopene | 300 mcg |
| Lutein | 250 mcg |
| Iodine | 150 mcg |
| Folic Acid | 800 mcg |
| Copper | 0.7 mg |
| Chromium | 120 mcg |
| Chloride | 58 mg |
| Calcium | 108 mg |
| Boron | 32 mcg |
| Biotin | 30 mcg |
| Iron | 6 mg |
| Tin | 10 mcg |

EXAMPLE 4

Method of Preparing the Nutritional Supplement

One exemplary multi-vitamin and mineral nutritional supplement comprising a plurality of vitamin and mineral nutritional supplement components and phytosterol was prepared using the following wet granulation method.

The phytosterol was delumped using a low energy oscillation system equipped with a screen. The delumped phytosterol was then transferred to a high shear granulator and combined with MgO, and dibasic calcium phosphate diluents (which are also actives), ZnO a low dose mineral active, microcrystalline cellulose, super disintegrant and polyvinyl pyrrolidine binder were added to the granulation bowl. Granulation was begun with a low speed blending and water was added gradually with mixing to form an acceptable granulation. One skilled in the art is familiar with the appearance and physical characteristics of an acceptable granulation.

Once an acceptable granulation was obtained the granulation was dried in a fluid bed dryer with air at an airflow inlet temperature of about 90° C. The granulation was dried to a moisture content of not more than about 1.5% w/w as determined by an infrared loss on drying balance.

The dried granulation was cooled and milled at a medium speed, with knives forward using a 0.050 screen. Approximately half of the milled granulation was put into a slant cone blender, followed by #20 mesh screened silicon dioxide. The remainder of the milled granulation was added and the mixture was blended.

Additional active ingredients and excipients including ascorbic acid and vitamin E acetate, dibasic calcium phosphate (a second portion), chromium chloride, sodium molybdate, stannous chloride, sodium metavanadate, nickelous sulfate, sodium selenate, manganese sulfate, Biotin, vitamin K, riboflavin, thiamine mononitrate, potassium iodide, niacinamide, copper sulfate, calcium pantothenate, pyridoxine hydrochloride, folic acid, cyanocobalamin, potassium chloride, ferrous fumarate, vitamin A acetate, beta carotene, vitamin $D_3$, lycopene, lutein, croscarmellose sodium, crospovidone, and microcrystalline cellulose (second portion) were added and blended for approximately 10 minutes. Magnesium stearate screened through a #20 mesh screen was added to the composition and blending continued for approximately 1.5 minutes.

The granulation thus obtained was compressed into tablets using tableting techniques known to those skilled in the art using a tablet tooling with an oval shape. The inventors believe that oblong, modified oval, and capsule shaped compacts may be easier for a consumer to swallow than round compacts of similar volume. In this embodiment a daily efficacious dosage of phytosterol and the indicated vitamins and minerals was tableted in two tablets each tablet having a volume of about 1.2 $cm^3$.

The tablets were then coated using an aqueous based film-coating system comprising polyvinyl alcohol.

Although the foregoing invention has been described in some detail by way of illustration and examples for purposes of clarity of understanding it will be obvious that certain changes and modifications may be practiced within the scope of the appended claims. Modification of the above-described modes of practicing the invention that are obvious to persons of skill or the art are intended to be included within the scope of the following claims.

We claim:

1. A nutritional supplement comprising a mixture of:
   (a) at least 3500 I.U. of vitamin A; at least 60 mg of vitamin C; at least 400 I.U. of vitamin D; at least 30 I.U. of vitamin E; at least 25 mcg of vitamin K; at least 1.5 mg of thiamin; at least 1.7 mg of vitamin $B_2$; at least 20 mg of niacin; at least 5 mg of vitamin $B_6$; at least 400 mcg of folic acid; at least 200 mcg of vitamin $B_{12}$; at least 30 mcg of biotin; at least 10 mg of pantothenic acid; at least 6 mg of pharmaceutically acceptable iron compound; at least 150 mcg of a pharmaceutically acceptable iodine compound; at least 40 mg of a pharmaceutically acceptable magnesium compound; at least 7.5 mg of a pharmaceutically acceptable zinc compound; at least 20 mcg of a pharmaceutically acceptable selenium compound; at least 0.7 mg of a pharmaceutically acceptable copper compound; at least 2 mg of a pharmaceutically acceptable manganese compound; at least 108 mg of a pharmaceutically acceptable calcium compound; at least 80 mg of a pharmaceutically acceptable phosphorus compound; at least 75 mcg of a pharmaceutically acceptable molybdenum compound; at least 32 mcg of a pharmaceutically acceptable boron compound; at least 5 mcg of a pharmaceutically acceptable nickel compound; at least 2 mg of a pharmaceutically acceptable silicon compound; at least 10 mcg of a pharmaceutically acceptable tin compound; at least 10 mcg of a pharmaceutically acceptable vanadium compound; at least 120 mcg of a pharmaceutically acceptable chromium compound; at least 64 mg of a pharmaceutically acceptable potassium compound; at least 58 mg of a pharmaceutically acceptable chloride compound; optionally at least 300 mcg of a pharmaceutically acceptable lycopene compound; optionally at least 250 mcg of a pharmaceutically acceptable lutein compound; and
   (b) phytosterol, wherein the phytosterol is in a free form and further the phytosterol is at least partially coated with silicon dioxide by ordered blending of the phytosterol with silicon dioxide, and wherein the nutritional supplement comprises at least 800 mg of the phytosterol and said amount is contained in 2-4 tablets of a tablet size suitable to be swallowed by a human; and wherein said tablet is prepared by a process comprising:
   (1) forming phytosterol particulate(s) of a suitable particle size; and then
   (2) mixing said phytosterol particulate(s) with silicon dioxide; and then
   (3) blending other suitable ingredients with phytosterol particulate(s) of step 2.

2. The nutritional supplement of claim 1, wherein the silicon dioxide is fumed silicon dioxide, precipitated silicon dioxide or a mixture thereof.

3. The nutritional supplement of claim 1, wherein the supplement is in the form of a tablet coated with a film coat comprising polyvinyl alcohol.

4. A method of a nutritional supplementation for a human which facilitates reduction of serum cholesterol comprising providing a human an effective amount of the nutritional supplement of claim 1.

5. A nutritional supplement comprising:
   800 mg to 3 g phytosterol in free form wherein the phytosterol is at least partially coated with silicon dioxide by ordered blending of the phytosterol with silicon dioxide, and said amount of phytosterol is contained in 2-4 tablets of a tablet size suitable to be swallowed by a human, wherein said tablet is prepared by a process comprising:
   (1) forming phytosterol particulate(s) of a suitable particle size; and then
   (2) mixing said phytosterol particulate(s) with silicon dioxide; and then
   (3) blending other suitable ingredients with phytosterol particulate(s) of step (2), wherein the ingredients comprise: 1300 I.U. to 12,000 I.U. of vitamin A; 0 mg to 250 mg of vitamin C; 200 I.U. to 2000 I.U. of vitamin D; 0 I.U. to 200 I.U. of vitamin E; 10 mcg to 90 mcg of vitamin K; 0.9 mg to 4.5 mg of thiamin; 0 mg to 5.1 mg of vitamin $B_2$; 5 mg to 40 mg of niacin; 1 mg to 8 mg of vitamin $B_6$; 0 mcg to 1400 mcg of folic acid; 2.4 mcg to 400 mcg of vitamin $B_{12}$; 0 mcg to 300 mcg of biotin; 0 mg to 16 mg of pantothenic acid; 0 mg to 18 mg of a pharmaceutically acceptable iron compound; 0 mcg to 300 mcg of a pharmaceutically acceptable iodine compound; 0 mg to 100 mg of a pharmaceutically acceptable magnesium compound; 3 mg to 15 mg of a pharmaceutically acceptable zinc compound; 0 mcg to 75 mcg of a pharmaceutically acceptable selenium compound; 0 mg to 10 mg of a pharmaceutically acceptable copper compound; 0 mg to 6 mg of a pharmaceutically acceptable manganese compound; 0 mg to 200 mg of a pharmaceutically acceptable calcium compound; 0 mg to 750 mg of a pharmaceutically acceptable phosphorus compound; 0 mcg to 250 mcg of a pharmaceutically acceptable molybdenum compound; 0 mg to 1.35 mg of a pharmaceutically acceptable boron compound; 0 mcg to 100 mcg of a pharmaceutically acceptable nickel compound; 0 mg to 40 mg of a pharmaceutically acceptable silicon compound; 0 mcg to 35 mcg of a pharmaceutically acceptable tin compound; 0 mcg to 25 mcg of a pharmaceutically acceptable vanadium compound; 0 mcg to 300 mcg of a pharmaceutically acceptable chromium compound; 0 mg to 125 mg of a pharmaceutically acceptable potassium compound; 0 mg to 120 mg of a pharmaceutically acceptable chloride compound; optionally 0 g to 3 g of omega-3 fatty acids; optionally 0 g to 3 g of a pharmaceutically acceptable lycopene compound; optionally 0 g to 3 g of a pharmaceutically acceptable zeaxanthin compound; and optionally 0 g to 3 g of a pharmaceutically acceptable lutein compound.

6. The nutritional supplement of claim 5, wherein the silicon dioxide is fumed silicon dioxide, precipitated silicon dioxide or a mixture thereof.

7. The nutritional supplement of claim 5, wherein the supplement is in the form of a tablet coated with a film coat comprising polyvinyl alcohol.

8. A method of a nutritional supplementation for a human which facilitates reduction of serum cholesterol comprising providing a human an effective amount of the nutritional supplement of claim 5.

* * * * *